United States Patent [19]

Robba et al.

[11] Patent Number: 4,673,675
[45] Date of Patent: Jun. 16, 1987

[54] 1-(2-PYRIDYL) 4-CYCLOALKYLMETHYL PIPERAZINES HAVING CARDIOTROPIC ACTIVITY

[75] Inventors: Max F. Robba; Michel E. Aurousseau, both of Paris, France

[73] Assignee: Innothera, France

[21] Appl. No.: 774,043

[22] Filed: Sep. 9, 1985

[30] Foreign Application Priority Data

Sep. 14, 1984 [FR] France ................ 84 14089

[51] Int. Cl.$^4$ ................ A61K 31/495; C07D 401/04; C07D 413/14
[52] U.S. Cl. ................ 514/252; 514/227; 544/121; 544/360; 549/362
[58] Field of Search ........... 544/121, 360; 514/252

[56] References Cited

U.S. PATENT DOCUMENTS 4,078,063  3/1978  Lumma et al. ............ 514/252
4,457,931  7/1984  Milani et al. ............ 544/360

FOREIGN PATENT DOCUMENTS 84993  8/1983  European Pat. Off. ......... 544/360
177392  4/1986  European Pat. Off. ......... 544/360

OTHER PUBLICATIONS

Milani et al., CA 101-23499n.

Primary Examiner—Donald G. Daus
Assistant Examiner—Cecilia Shen
Attorney, Agent, or Firm—Schiller, Pandiscio & Kusmer

[57] ABSTRACT

Compounds of formula:

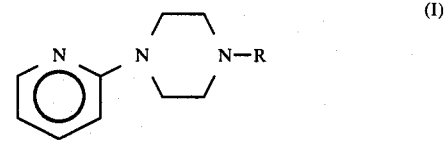

in which R represent
 a cycloalkylmethyl group;

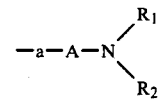

group where —A— symbolizes a hydrocarbon chain and $R_1$ and $R_2$ each designate an alkyl group or form jointly with N a heterocyclic radical;
an anilinocarbonylmethyl group whose phenyl nucleus is possibly substituted; or
a substituted benzyl group.

These compounds are useful as drugs having cardiotropic activity.

10 Claims, No Drawings

1-(2-PYRIDYL) 4-CYCLOALKYLMETHYL PIPERAZINES HAVING CARDIOTROPIC ACTIVITY

The present invention relates to novel 1-(2-pyridyl) piperazines substituted in position 4 and the salts thereof, as well as the process for preparing these compounds and the therapeutical application thereof.

The new piperazines of the invention correspond more precisely to the general formula:

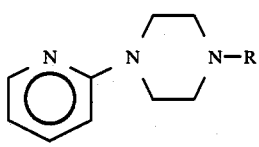 (I)

in which R represents:

a cycloalkylmethyl group with 4 to 7 carbon atoms;

a group of structure

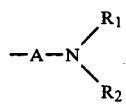

where the pair [A, NR$_1$R$_2$]=[CH$_2$CH$_2$, N(iPr)$_2$], [CH$_2$C$_2$, perhydroazepino], [CH$_2$CH$_2$CH$_2$, N(C$_2$H$_5$)$_2$], [CH$_2$CH$_2$CH$_2$, pyrrolidino], [CH$_2$CH$_2$CH$_2$, perhydroazepino], [CH$_2$C$_2$CH$_2$, morpholino], [CH$_2$CH$_2$CH$_2$, 2,6 dimethyl morpholino] or [CH(CH$_3$)CH$_2$, N(C$_2$H$_5$)$_2$];

an anilinocarbonylmethyl group whose phenyl nucleus is possibly substituted by one or more fluorine atoms or by one or more trifluoromethyl groups; or a benzyl group substituted by the methylenedioxy chain or by one or more methoxy groups and also possibly by a halogen atom.

The present invention further relates to the addition salts of the compounds (I) with mineral acids such as hydrochloric acid, sulfuric acid and phosphoric acid or with organic acids such as oxalic acid, maleic acid, citric acid or methanesulfonic acid.

The present invention also relates to the process for preparing the compounds (I) and salts thereof, which process consists in condensing 1-(2-pyridyl) piperazine of formula:

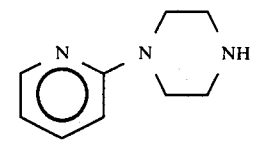 (II)

with a derivative of formula:

$$R-X \quad \text{(III)}$$

where R has the same meaning as in formula (I) and X represents a good leaving electrophile group, more particularly a bromine or chlorine atom or a mesyloxy or tosyloxy group.

This condensation is preferably carried out in the hot in an inert organic solvent such as isopropylic alcohol, ethyl acetate or dimethylformamide. An acid neutralization agent, such as sodium or potassium carbonate for example, may also be present.

As for the salts of compounds (I), they are obtained quite conventionally by reaction with an organic or mineral acid, preferebly at reflux in an appropriate inert solvent such as acetone or methanol for example.

The following preparation is given by way of example to illustrate the invention.

EXAMPLE 1-(2-pyridyl) 4-cyclopropylmethyl piperazine(1)

To a solution of 25 g (0.153 mole) of 1-(2-pyridyl) piperazine in 45 ml of dimethyl formamide are added 16.2 g (0.153 mole) of sodium carbonate. The suspension is vigorously stirred and heated to 60° C. Then 20.7 g (0.225 mole) of chloromethylcyclopropyl is added drop by drop, then heated for 4 hours at 80° C. with stirring. After cooling, 200 ml of water are added then the aqueous phase is extracted thrice with 100 ml of ethyl ether. The combined ether phases are washed, dried on anhydrous disodic sulfate then dry concentrated in a vacuum. Thus 30 g (yield: 90%) of a yellow oil are obtained formed by the expected compound.

Monooxalate (1a)

The monooxalate is obtained by reacting the 1-(2-pyridyl) 4-cyclopropylmethyl piperazine base with an equivalent of oxalic acid by heating at reflux in acetone for 1 hour. After crystallization in acetonitrile, this salt is in the form of white crystals melting at 198° C.

Bis hydrochloride (1b)

The bis hydrochloride is obtained by reacting the 1-(2-pyridyl) 4-cyclopropylmethyl piperazine base with a hydrochloric acid solution in methanol. After crystallization in isopropylic alcohol, this salt has a melting point of 265° C.

The compounds appearing in table I herebelow are prepared using similar operating conditions as for the above example.

TABLE I

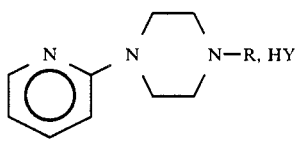

| Compound no. | R | HY | Reaction conditions | Melting point (°C.) | Crystallization Solvent | Yield (%) | Empirical formula |
|---|---|---|---|---|---|---|---|
| 2 | CH₂—◇ (cyclobutyl) | 1.5 (COOH)₂ | DMF, reflux 17h RX = RBr | 179 | Acetonitrile (1): methanol (1) | 95 | $C_{17}H_{24}N_3O_6$ |
| 3 | CH₂—(cyclohexyl, H) | 2 (COOH)₂ | DMF, reflux 17h RX = RBr | 178 | Acetonitrile | 90 | $C_{20}H_{29}N_3O_8$ |
| 4 | (CH₂)₂N(CH(CH₃)₂)₂ | 3 (COOH)₂ | Reflux, 17h isopropanol RX = RCl | 157 | Ethanol (95%) | 95 | $C_{23}H_{36}N_4O_{12}$ |
| 6 | (CH₂)₂N-(pyrrolidinyl) | 3 (COOH)₂ | Reflux, 17h isopropanol RX = RCl | 200 | Ethanol (80%) | 90 | $C_{23}H_{34}N_4O_{12}$ |
| 7 | (CH₂)₃N(C₂H₅)₂ | 3 (COOH)₂ | Reflux, 17h isopropanol RX = RCl | 195 | Ethanol (70%) | 90 | $C_{22}H_{34}N_4O_{12}$ |
| 8 | (CH₂)₃N-(piperidinyl) | 3 (COOH)₂ | Reflux, 17h isopropanol RX = RCl | 188 | Ethanol (50%) | 95 | $C_{22}H_{32}N_4O_{12}$ |
| 10 | (CH₂)₃N-(pyrrolidinyl) | (COOH)₂ | Reflux, 17h isopropanol RX = RCl | 187 | Ethanol (95%) | 90 | $C_{20}H_{32}N_4O_4$ |
| 11 | (CH₂)₃N-(morpholinyl, O) | 2 (COOH)₂ | Reflux, 17h isopropanol RX = RCl | 196 | Ethanol (95%) | 70 | $C_{20}H_{30}N_4O_9$ |
| 12 | (CH₂)₃N-(2,6-dimethylmorpholinyl) | 2 (COOH)₂ | Reflux, 17h isopropanol RX = RCl | 201 | Ethanol (50%) | 95 | $C_{22}H_{34}N_4O_9$ |
| 13 | CH(CH₃)CH₂—N(C₂H₅)₂ | 3 (COOH)₂ | Reflux, 17h isopropanol RX = RCl | 163 | Ethanol (95%) | 90 | $C_{22}H_{34}N_4O_{12}$ |
| 14 | CH₂CONH—(3-F-phenyl) | 1 (COOH)₂ | Reflux, 4h DMF | 158 | Ethanol (1): Acetonitrile (1) | 70 | $C_{19}H_{21}FN_4O_5$ |

TABLE I-continued

[Structure: benzene ring fused/attached to N, N, piperazine ring with N—R, HY]

| Compound no. | R | HY | Reaction conditions | Melting point (°C.) | Crystallization Solvent | Yield (%) | Empirical formula |
|---|---|---|---|---|---|---|---|
| 15 | CH$_2$CONH-(3,5-difluorophenyl) | 1 (COOH)$_2$ | Reflux, 4h DMF RX = RCl | 199 | Methanol (1): Acetonitrile (1) | 70 | C$_{19}$H$_{20}$F$_2$N$_4$O$_5$ |
| 16 | CH$_2$CONH-(3-CF$_3$-phenyl) | 2 (COOH)$_2$ | Reflux, 4h DMF RX = RCl | 183 | Methanol (1): Acetonitrile (1) | 70 | C$_{22}$H$_{23}$F$_3$N$_4$O$_5$ |
| 17 | CH$_2$-(2,4,5-trimethoxyphenyl) | 2 (COOH)$_2$ | Reflux, 4h DMF RX = RCl | 191 | Acetonitrile | 95 | C$_{23}$H$_{29}$N$_3$O$_{11}$ |
| 18 | CH$_2$-(chloro-methylenedioxyphenyl) | 1 (COOH)$_2$ | Reflux, 3h DMF RX = RCl | 213 | Acetonitrile | 95 | C$_{19}$H$_{20}$ClN$_3$O$_6$ |

The compounds (I) of the invention and the pharmaceutically acceptable salts thereof were tested on laboratory animals and showed pharmacological properties and more especially a cardiotropic and particularly positive inotropic and bradycardizing activity.

A. In vitro demonstration of the bradycardizing effect

The bradycardizing effect was revealed by studying the chronotropic action on the isolated right auricle of a guinea pig.

Guinea pigs of either sex were killed with a blow and bled, the right auricle was swiftly removed and immediately immersed in a Krebs-Henseleit solution, thermostatically controlled to 36° C.±0.5° C. and aerated with a mixture of O$_2$ and CO$_2$ (95% and 5%). The preparation was connected to an isometric myograph (F-50 Narco) then to a recording system (Physiograpg M-K III—Narco).

A 60 minute delay was required for ensuring chronotropic action stability.

The compounds (I) of the invention and the pharmaceutically acceptable salts thereof were added to the nutritive medium in a concentration of 1.10$^{-4}$ g.ml$^{-1}$ and left in contact with the auricle for 30 minutes. The action was evaluated by the percentage reduction of the number of beats/minute (beat/min.) before administration of the compound under test.

The results are shown in the following table II.

TABLE II

Bradycardizing activity of the compounds of the invention studied on the isolated right auricle of a guinea pig.

| No. of compound tested | Reduction of the chronotropic effect at the concentration of $1 \cdot 10^{-4}$ g · ml$^{-1}$ % |
|---|---|
| 1a | 24 |
| 2 | 7 |
| 3 | 13 |
| 4 | 9 |
| 6 | Arrhythmia |
| 7 | 16 |
| 8 | 20 |
| 10 | 0 |
| 11 | Arrhythmia |
| 12 | 0 |
| 13 | Arrhythmia |
| 14 | 18 |
| 15 | 0 |
| 16 | 18 |
| 17 | 31 |
| 18 | 11 |

B. In vitro and in vivo demonstration of the positive inotropic effect

1. In vitro study

The in vitro study was made on the contractile force of the isolated left auricle of a guinea pig. The technique used was that of P. LUMBEY et Coll. (Cardiovascular Research, II, 17-25, 1977). It allowed the cardiac inotropic function $\beta_1$ to be studied.

Guinea pigs of either sex were killed with a blow and bled, the left auricle being swiftly removed and immersed immediately in a Krebs-Henseleit solution, thermostatically controlled to 36° C. and aerated with an $O_2$ and $CO_2$ mixture (95% and 5%). The preparation was connected to an isometric myograph (F-50 Narco), then to a recording system (Physiograph M-K III Narco). For the whole duration of the test the auricle was electrically stimulated by a neurostimulator (Equipement Industriel II) at the frequence of 90 to 120 beats/min.

The agonists, i.e. the reference product and the compounds of the invention were added to the nutritlive medium according to the cumulative method of VAN ROSSUM (Arch. Inter. Pharmacodyn, 143, 299–330, 1963).

The quantification of the positive inotropic effect by calculating the $pD_2$ (according to E. J. ARIENS and J. M. VAN ROSSUM—Arch. Intern. Pharmacodyn. CX, no. 2, 2, 19 and Arch. Inter. Pharmacodyn. 143, 299–330, 1963) which characterizes the affinity of the tested compound for the receptors as well as the intrinsic activity ($\alpha$) which defines the relative power of the agonist with respect to a reference product (Dopamine) were determined.

The results obtained by way of example with compound 1a of the invention are given in table III herebelow.

TABLE III

Inotropic activity of compound 1a on the isolated auricle of a guinea pig

| Product | $pD_2^{(a)}$ | $Kb^{(b)}$ | $\alpha^{(c)}$ |
|---|---|---|---|
| 1a | 4.68 ± 0.42 | $2.09 \cdot 10^{-5}$ M | 0.60 ± 0.30 |
| DOPAMINE (reference product) | 5.13 ± 0.18 | $7.41 \cdot 10^{-6}$ M | 1.00 |

$^{(a)}pD_2$ = negative log. of the molar concentration of the agonist which produces an effect equal to 50% of its maximum action.
$^{(b)}Kb$ = molar concentration of the agonist which produces an effect equal to 50% of its maximum action.
$^{(c)}\alpha$ = ratio between the maximum effect of an agonist and the maximum effect of the reference agonist ($\alpha = 1$)

2. In vivo study

The positive inotropic effect of compounds (I) of the invention and the pharmaceutically acceptable salts thereof were further tested on the cardiac dynamics of an anaesthetized animal and on a wakeful chronically implanted animal.

a. Test on a dog anaesthetized with Nembutal

Two test protocols were carried out, one on a dog with open thorax and the other on a dog with closed thorax. The left intraventricular pressure (PIVG) and aortic pressure (supra sigmoid) (PAO) were measured with high fidelity micro-sensors (Millar 5F), the first derivative of the left ventricular pressure (dP/dt) was recorded as well as the electrocardiogram. The instantaneous alveolar $PCO_2$ was continuously measured. Finally, different blood flow rates were measured, namely the femoral and carotid flow rates in the animals with closed thorax and the aortic and coronary flow rates in those on which a thoracotomy had been performed. These different rates were measured by the electro-magnetic method.

RESULTS

Test on animals with open thorax

By way of examples, two doses of compound 1a were tested; 0.5 and 1 mg.kg$^{-1}$ i.v. The results are given in table IV hereafter.

Fo the 0.5 mg.kg$^{-1}$ i.v. dose, the aortic flow rate increased significantly by 21% and the same for the systolic ejection volume which increased 16%, the acme of the action being situated 45 minutes after injection. A non-significant increase of 15% of the dP/dt was observed. Concurrently, the left ventricular telediastolic pressure decreased significantly (28%).

The other parameters measured did not vary significantly.

For the 1 mg.kg$^{-1}$ i.v. dose, the results were approximately the same as those observed for the smaller dose, except for the dP/dt which increased significantly (+31%) for the 90 minutes following injection.

Test on animals with closed thorax

An analysis of the dose/effect relation on three dogs (see results shown in table V below) confirmed the results obtained on dogs with open thorax for compound 1a.

The acme of the positive inotropic effect of compound 1a appeared with the 0.5 mg.kg$^{-1}$ i.v. dose, increasing the dose did not increase the effect. The positive inotropic activity in animals with closed thorax is stronger for a dose of 0.5 mg.kg$^{-1}$ i.v. than in animals with open thorax; there is a maximum increase of the dP/dt+ of 52%. The duration of the positive inotropic effect exceeds three hours.

It should be emphasized that compound 1a has an appreciable and durable respiratory analeptic effect.

TABLE IV

Effect of compound 1a on the cardiac hemodynamics in anaesthetized dogs (number of animals used for the test: 3)
Animals with open thorax

| | Modification 0.5 mg · kg$^{-1}$ i.v. (%) | Modification 1 mg · kg$^{-1}$ i.v. (%) |
|---|---|---|
| D.A.O.$^{(a)}$ | +21 | +23 |
| V.E.S.$^{(b)}$ | +16 | +13 |
| dP/dt+$^{(c)}$ | +15 | +31 |

TABLE V

Effect of compound 1a on the cardiac hemodynamics of anaesthetized dogs (number of animals used for the test: 3)
Animals with closed thorax

| | Modification 0.5 mg · kg$^{-1}$ i.v. (%) | Modification 2 mg · kg$^{-1}$ i.v. (%) |
|---|---|---|
| P.Ao m$^{(d)}$ | +11 | +8 |
| dP/dt+$^{(c)}$ | +52 | +28 |
| PtdVG$^{(e)}$ | −35 | −31 |

$^{(a)}$D.A.O.: aortic flow rate
$^{(b)}$V.E.S.: systolic ejection volume
$^{(c)}$dP/dt+: first derivative of the left ventricular pressure
$^{(d)}$P.Ao m: average aortic pressure
$^{(e)}$: left ventricular telediastolic pressure b. Test on chronically implanted wakeful dogs The compounds were tested orally and intravenously on dogs previously implanted with a pressure probe placed in the left ventricle (Janssen) and a Doppler rate sensor placed on the aorta, the tests being carried out at the minium 8 days after implantation.

RESULTS

Orally (see table VI)

Compound 1a was tested at two doses: 5 and 10 mg.kg$^{-1}$ (orally). An increase of the cardiac performances was observed shown by the increase of the dP/dt+ (57%) of the dP/dt+/P) (32%) and of the aortic flow rate (27%). Concurrently, the cardiac frequency increased by 31%.

The results were approximately similar for both doses.

Intravenously

Compound 1a was tested at 2 doses: 0.5 and 1 mg.kg$^{-1}$. The effect seems, in this case, to depend on the dose and is characterized, as for the oral dose, by an increase of the performances of the cardiac dynamics, the increase of the dP/dt+ reaching 136% for the 1 mg.kg$^{-1}$ dose.

TABLE VI

Effect of compound 1a on the cardiac hemodynamics in chronically implanted wakeful dogs (number of animals for the test: 3).

| Chronically implanted unanaesthetized dog | Modification 5 mg · kg$^{-1}$ p.o. (%) | Modification 10 mg · kg$^{-1}$ p.o. (%) |
|---|---|---|
| dP/dt+[a] | +57 | +55 |
| D.A.O.[b] | +27 | +27 |
| PIVG Syst.[c] | +15 | +26 |
| F.C.[d] | +31 | +45 |

[a]dP/dt+: first derivative of the left ventricular pressure
[b]D.A.O.: aortic flow rate
[c]PIVG Syst.: systemic left intraventricular pressure
[d]F.C.: heartbeat rate The toxicity of the compounds of the invention was also tested. It concerns more precisely the test of toxicity by a single administration made for all the compounds on male mice, E.O.P.S. of SWISS strain (5 animals per batch).

The compounds under test were solubilized in a 9% aqueous solution of NaCl, at various concentrations and the solutions obtaoned were injected intravenously at the rate of 10 ml.kg$^{-1}$ of body weight.

The administration was made in 20 seconds, the animals being kept under clinical observation for 3 hours after administration, then daily for 7 days.

The 50% lethal doses (LD$_{50}$ mg.kg$^{-1}$) were calculated by the method of Litchfield et Wilcoxon (J. Pharm. Exp. Therap., 96-99, 1949) from the different mortalities noted.

The results of this test are shown in table VII.

TABLE VII

Toxicity by a sigle intravenous administration in mice.

| No. of the compounds | LD$_{50}$ mg · kg$^{-1}$[a] 95% confidence limit | Clinical symptomatology[b] |
|---|---|---|
| 1a | 47 (43–52) | Sedation, then Straub's phenomenom, cries, convulsions |
| 2 | 67 (58–78) | Somersaults, convulsions, salivation |
| 3 | 81 (74–89) | Hypersensitivity, stereotypy |
| 4 | 95 (87–104) | Cyanosis, starts |
| 6 | 84 (78–91) | Convulsions, jumps, Straub's phenom. |
| 7 | 96 (81–113) | Cyanosis, apnoea |
| 8 | 142 (129–156) | Polypnoea, agitation, stereotypy |
| 10 | 74 (67–82) | Apnoea, convulsions, hypersensitivity |
| 12 | 149 (136–163) | Convulsions, Straub's phenom., trembling, salivation |
| 13 | 76 (64–90) | Hypersensitivity, exophthalmy, beginning of convulsions |
| 14 | 129 (118–141) | Apnoea, sedation |
| 16 | 109 (99–121) | Apnoea, Straub's phenom., convulsions, somersaults, salivation, lacrymation |
| 17 | 130 (122–139) | Apnoea, Straub's phenom., |

TABLE VII-continued

Toxicity by a sigle intravenous administration in mice.

| No. of the compounds | LD$_{50}$ mg · kg$^{-1}$[a] 95% confidence limit | Clinical symptomatology[b] |
|---|---|---|
| | | convulsions |

[a]LD$_{50}$ calculated by the method of Litchfield and Wilcoxon
[b]Clinical symptoms observed at the dose where there was no mortality The pharmacological test herebefore shows the therapeutical interest of the compounds (I) and of the pharmaceutically acceptable salts thereof. These compounds and salts find then their application as drugs for man and animals in particular for treating heart diseases and more particularly cardiac insufficiencies (failures and troubles characterized by a too low cardiac flow rate).

The present invention further extends to the pharmaceutical compositions containing at least one of the compounds (I) and pharmaceutically acceptable acid addition salts of these compounds (I), as well as one or more pharmaceutically acceptable vehicles. These compositions may be formulated more especially in view of oral administration thereof and will then be in the form of sugar coated pills, capsules, tablets or drinkable solutions, or with a view to parenteral administration thereof and are then in the form of injectable solutions, the methods of preparing these different forms being well known to a man skilled in the art.

The drugs and pharmaceutical compositions of the invention may be administered, in one or more daily doses corresponding to a total amount of active ingredient which may go from 5 mg to 1 g.

We claim:

1. A chemical compound having the formula

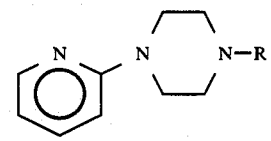

(1)

and the mineral or organic acid addition salts thereof, wherein R is a cycloalkylmethyl group of 4 to 7 carbon atoms.

2. A compound according to claim 1, wherein R is 4-cyclopropylmethyl.

3. A compound according to claim 2, wherein said compound is a monooxalate salt.

4. A compound according to claim 2, wherein said compound is a bis hydrochloride salt.

5. A compound according to claim 1, wherein R is 4-cyclobutylmethyl.

6. A compund according to claim 5, wherein said compound is a 1.5 oxalate salt.

7. A compound according to claim 1, wherein R is 4-cyclohexylmethyl.

8. A compound according to claim 7, wherein said compound is a bis oxalate salt.

9. A pharmaceutical composition having a cardiotropic, isotropic or bradycardizing activity comprising (a) a therapeutically effective amount of a compound according to claim 1, and (b) a pharmaceutically acceptable carrier.

10. A method for treating a human or an animal for heart disease which comprises the step of internally administering thereto a therapeutically effective amount of a compound according to claim 1.

* * * * *